United States Patent [19]

Haas et al.

[11] Patent Number: 4,618,772

[45] Date of Patent: Oct. 21, 1986

[54] NUCLEAR IMAGING APPARATUS

[75] Inventors: Werner J. Haas, Uttenreuth, Fed. Rep. of Germany; Rainer L. Haerten, Long Grove, Ill.

[73] Assignee: Siemens Gammasonics, Inc., Des Plaines, Ill.

[21] Appl. No.: 693,493

[22] Filed: Jan. 22, 1985

Related U.S. Application Data

[63] Continuation-in-part of Ser. No. 381,143, May 24, 1982, abandoned.

[51] Int. Cl.$^4$ ............................................. G01T 1/166
[52] U.S. Cl. ................................................. 250/363 S
[58] Field of Search .................... 250/363 SF, 363 SC, 250/363 SR

[56] References Cited

U.S. PATENT DOCUMENTS

| | | | |
|---|---|---|---|
| 3,011,057 | 11/1961 | Anger | 250/363 SR |
| 3,732,419 | 5/1973 | Kulberg et al. | 250/366 |
| 3,852,603 | 12/1974 | Muehllehner | 250/369 |
| 4,223,222 | 9/1980 | Gray et al. | 250/363 SF |
| 4,254,338 | 3/1981 | Abel et al. | 250/340 |
| 4,417,143 | 11/1983 | Haas et al. | 250/363 SC |

FOREIGN PATENT DOCUMENTS 24280 2/1984 Japan ............................ 250/363 SR

OTHER PUBLICATIONS

H. Handmaker, J. M. Lowenstein "Nuclear Imaging with a Mobile Gamma Camera System" *Electromedica* (Mar. 1976).

*Primary Examiner*—Constantine Hannaher
*Attorney, Agent, or Firm*—Mark H. Jay

[57] ABSTRACT

A scintillation camera receives radiation from an object under examination and determines the locations of scintillation events. The camera issues x and y coordinate signals which correspond to these locations, and z unblank signals which correspond to the intensity of the scintillation events. Preferably, the scintillation camera can be moved along arc-shaped scanning paths. It is possible to generate a shift movement between the object and the scintillation camera between various pass positions. The output signals of the scintillation camera are forwarded to a display device via an electronic circuitry which encloses a square field of view. This square field of view has a fixed angular orientation with respect to a fixed coordinate system during each of the aforementioned arc-shaped scanning passes.

13 Claims, 9 Drawing Figures

NUCLEAR IMAGING APPARATUS

CROSS REFERENCE TO RELATED APPLICATION

This application is a continuation-in-part of application Ser. No. 381,143 filed May 24, 1982, now abandoned.

BACKGROUND OF THE INVENTION

1. Field of the Invention

This invention relates to apparatus and a method for producing nuclear images of an object under examination. More particularly, this invention relates to nuclear imaging by means of a scintillation camera. Still more particularly, this invention relates to a whole-body scanning apparatus and a method for obtaining nuclear images from a patient.

2. Description of the Prior Art

Scintillation cameras such as the Anger gamma camera (U.S. Pat. No. 3,011,057) are in wide use for producing nuclear images of a patient under examination. Of particular interest are whole-body images of the patient. Whole-body imaging using gamma cameras is performed either by a linear scanning movement of the camera along the patient table, or by a linear scanning movement of the patient table whereby the camera is kept stationary (see brochure "Whole-body Accessory, Models 3222, 3, 4, 5" by Siemens Corporation, Iselin, N.J.; see book "Nuclear Medicine, Technology and Technques", published by the C. V. Mosby Co., St. Louis, Toronto, London (1981), pp. 389-397; see brochure C46A "Pho/Gamma Rota, Introductory Data" by Siemens Gammasonics, Inc.) Scanning is performed in one or more passes.

For data acquisition and imaging a rectangular field of view is produced by masking the camera's field of view either electronically or mechanically. This is done in order to keep the sensitivity of the imaging apparatus constant throughout the scanned area. There are three major disadvantages using this linear scanning technique:

1. There is a trade-off between the scan width of the scanning field of view and the sensitivity of the apparatus. With the scan width chosen large, the scanning field of view has to be small and the scanning speed has to be slow in order to intergrate a number of radiation counts which is sufficiently large for generating a sharp image. With the selection of a wide scanning field of view, or a high scanning speed, the scan width has to be made small.
2. When multiple passes are required to produce the image of the object under examination, faint longitudinal lines appear on the image. These "zipper lines" are generated at the border between the areas covered by adjacent passes. A "zipper line" is due to a slight separation or gap between the areas covered by each pass. Alternately, there may be slight overlaps. The "zipper lines" are irritating in the evaluation of the images.
3. Usually there are high mechanical and installation costs as well as large space requirements.

Electronical rotation of x and y voltage coordinates in nuclear medicine imaging is disclosed in Phys. Med. Biol., 1977, vol. 22, no. 6, pp. 1202-1206, in particular in FIG. 1 on p. 1203.

SUMMARY OF THE INVENTION

1. Objects

It is an object of this invention to provide a method and an apparatus for producing nuclear images in which a comparatively large scan width and a high sensitivity are obtained at the same time.

It is another object of this invention to provide a method and an apparatus for nuclear imaging wherein the zipper line between neighboring passes is avoided.

It is still another object of this invention to provide a method and an apparatus for nuclear imaging which requires a relatively small space.

2. Summary

According to this invention, a nuclear imaging apparatus for producing images of an object under examination is provided. This apparatus produces images according to nuclear radiation emitted by the object.

The apparatus contains a scintillation camera such as an Anger camera for receiving the radiation and for determining the locations of scintillation events which are caused by the nuclear radiation in the scintillator of the camera. The scintillation camera issues x and y coordinate signals which are indicative of the locations of the scintillation events. It also issues unblank z signals which indicate that the energy of the scintillation events was found to be within a certain preset energy discriminator window.

The apparatus also contains a display device provided with a display screen. Each unblank z signal enables the electron beam of the display device to write an image point on a screen location which is determined by the associated x and y coordinate signals.

The apparatus further contains a device for generating a relative movement between the scintillation camera and the object along arc-shaped scanning paths. Thus, the object can be scanned along portions of circles having predetermined length and radius. Preferably, the camera is rotated about a rotation axis and thereby moved with respect to the object under examination.

The apparatus also contains a transferring device for transferring the camera or the object from at least a first pass position to a second pass position. This transfer is performed in a linear shift direction. Each of the first and second pass positions may be a starting point or an end point of a pass along one of the aforementioned arc-shaped scanning paths. Generally, the devices for generating the scanning movement and the shifting movement are designed such that the scintillation camera can scan the object in two or more passes along parallel arc-shaped scanning paths.

The apparatus further contains an electronic device which is supplied with x and y coordinate signals. This electronic device encloses or defines a rectangular field of view in the generally circular field of view of the camera. The output signal of the electronic device may be used to disable the unblank z signal whenever at least one of the associated x and y signals is found to be outside of said rectangular field of view. Alternatively, the electronic device may be designed such that an x or y signal is not transmitted to the display device in case the respective x or y coordinate signal is outside the rectangular field of view. In particular, the electronic device generates a square field of view. This square field of view maintains a fixed angular orientation with respect to a coordinate system which is fixed in space when the scintillation camera scans the object under examination. This feature is obtained by electronic coordinate transformation means contained in the electronic device.

According to this invention, a method for producing images of an object under examination by means of a scintillation camera which generates a rectangular, or preferably a square field of view on a display device comprises the steps of scanning the object in a plurality of parallel overlapping passes, whereby in each pass the orientation of the field of view is maintained with respect to a coordinate system which is fixed in space. Thus, the field of view in a first pass overlaps the field of view in an adjacent second pass. Using a design performing an arc scan instead of the linear scan according to the prior art simplifies the mechanical installation.

The foregoing and other objects, features and advantages of the invention will be apparent from the following more particular description of preferred embodiments of the invention, as illustrated in the accompanying drawings.

DETAILED DESCRIPTION OF THE PREFERRED EMBODIMENTS

Figure 1:
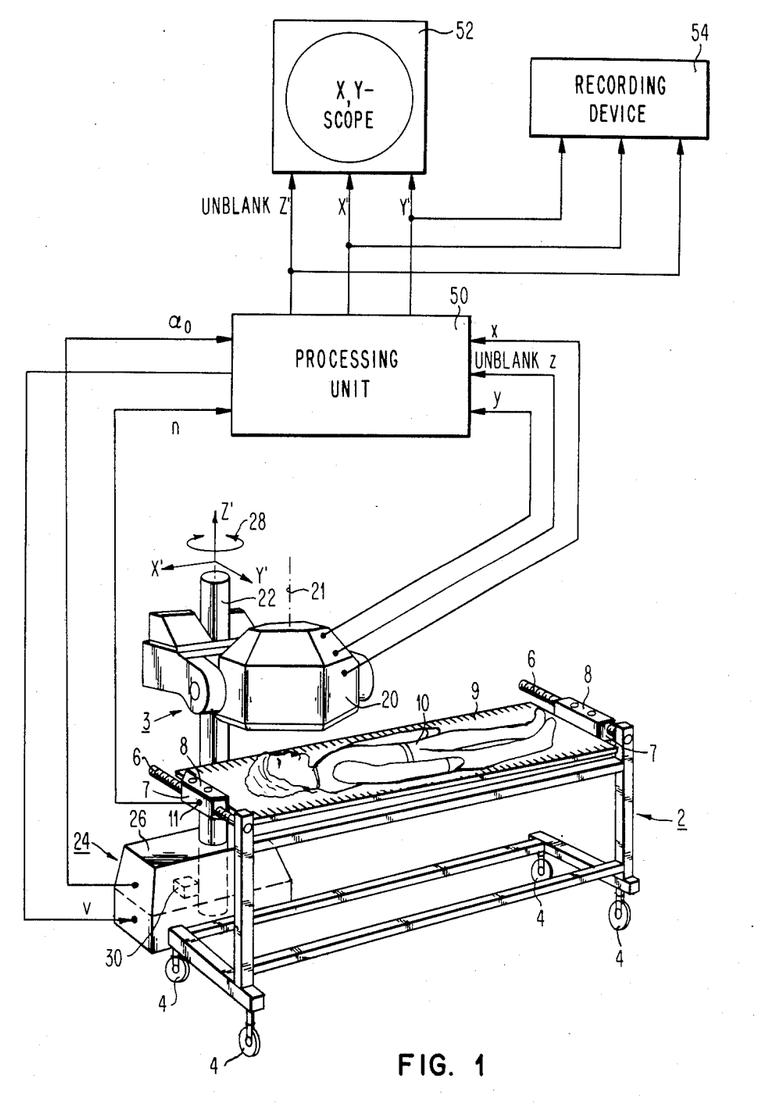
FIG. 1 is a perspective overview of a whole-body scanning apparatus for producing nuclear images according to a first embodiment of the invention.

In FIG. 1, an embodiment of a nuclear imaging apparatus or whole body arc scanner for gamma radiation is illustrated. The scanner comprises a movable trolley or patient supporting table 2 and a scintillation camera system 3.

The patient table 2 contains a conventional framework which is supported by coasters 4. The framework has attached thereto two horizontal guiding rails 6 arranged parallel to each other and having free outer ends. On these rails 6 supporting members 7 are slidably secured. On the supporting members 7 Z-shaped plates 8 are mounted. These plates 8 support a table top 9. Due to the sliding members 7, the table top 9 is movable in the Y' direction of a fixed orthogonal coordinate system X', Y', Z'. The longitudinal axis of the table top 9 extends in the X' direction of the coordinate system X', Y', Z'. The vertical axis is termed Z'. The table top 8 is designed for carrying a patient 10 to be examined.

During an examination of the patient 10, the patient supporting table 2 is fixed, i.e. immovable, in the examination room. However, the top 9 of the table 2 can be moved transversely to its longitudinal direction, that is in linear Y' direction, before and/or after an arc scan, which arc scan will be explained hereafter. To this end, the supporting members 8 traveling on the guiding rails 6 are shifted in Y' direction.

Such shift from a first to a second position can be performed either manually or by a motor (not shown). Shifting is preferably in a step by step fashion, whereby the shifting distance between any two adjacent positions is the same.

One of the supporting members 7 contains a position encoder generally designated by 11. This position encoder 11 issues a signal which is a measure of the table position with respect to the Y direction. The encoder 11 is of conventional design. In the present embodiment, the table position is represented by n, whereby n is one of the integers 1, 2, ... k.

Thus, the length of the guiding rails 6 is divided into k discrete and firm positions. Adjacent positions have the same distance from each other. For instance, k=5 distinct positions n=1, 2, ... 5 can be used. Subsequently the discrete positions will be termed "pass positions".

The movable scintillation camera system 3 contains a conventional scintillation camera 20 supported by a camera column 22. The camera axis is designated by 21. A scintillation camer 20 is a widely used nuclear medical diagnostic device. A scintillation camera such as the one shown in U.S. Pat. No. 3,011,057 (Anger) or in U.S. Pat. No. 3,732,419 (Kulberg et al) are examples of scintillation cameras which may be used. In certain applications, preferably a large field of view gamma camera may be applied.

The gamma camera 20 is attached to a column 22 which is positioned in Z' direction. The camera face is directed toward the patient 10 and the camera axis 21 is adjusted vertically. The column 22 is supported by a stand 24 which includes a box-shaped housing 26. As will be explained with respect to FIG. 8, the stand 24 may be moveable by any suitable means in X' direction, that is perpendicularly to the moving diection of the table top 9. To this end, the stand 24 may contain a driving motor, a gear system, and a motor control device (not shown).

In order to perform a rotational movement about the vertical Z' axis of the column 22 the box 26 contains a sprocket and motor, or some other driving mechanism (not visible in FIG. 1) for driving the column 22. Thus, the camera head 20 can be pivoted about the Z' axis along an arc-shaped scanning path. This pivoting movement is indicated by a curved double arrow 28.

The stand 24 also contains a column position sensor 30, the output signal of which is representative of the angular position $\alpha_0$ of the column 22. Thus, the sensor 30 measures the angular column position $\alpha_0$. Any suitable sensor 30 applicable for sensing the position of a rotational movement can be used.

The signals representing the column position $\alpha_0$ and the table position n (e.g. n=1, 2, ... k) are transmitted to a processing unit 50. In addition, coordinate signals x, y and unblank signals z issued by the camera 20 are transmitted to the processing unit 50. At the output of this unit 50, output signals X' and Y' and an unblank signal Z' are furnished. These output signals X' and Y' and the unblank signal Z' associated therewith are transmitted to a display device 52 having a screen, such as an (x, y)-A-scope or a (x, y)-persistence scope, both of conventional design. The display device 52 may be preferably an electronically simulated persistence scope. The unblank signal Z' enables the display of image points on screen locations determined by the X' and Y' signal.

The output signals X', Y' and the unblank signal Z' are also transmitted to a recording device 54 for image storage purposes. After a desired period of the time, the number of scintillation events accumulated and stored at each position X', Y' can be used for display on the screen of the display device 52. The image points correlated with X', Y' signals can be integrated over the scanning time (given by preselected scanning speed) i.e., using the aforementioned (x, y)-A-scope and a photographic camera.

In using the scintillation camera 20, a medical technician commonly injects a fluid containing a radio nuclide into the patient's blood. After a certain time, the technician monitors the distribution of the radio-isotope in the patient for such purposes as monitoring the propensity of organs or tissue to absorb isotope containing components of the fluid.

The scintillation camera 20 is positioned adjacent to the patient 10 in such a position that radioactive emissions from the isotope impinge thereupon. Commonly, the camera 20 is designed to monitor gamma radiation.

The scintillation camera 20 includes a flat scintillation crystal or plate, any position on which can be described by a pair of x, y coordinates. Each time a radiation quantum impinges on the scintillation plate, it fluoresces with a characteristic intensity. Electronic circuitry contained in the camera 20 senses the fluorescence and produces analog signals, that is the aforementioned x and y coodinate signals, which are indicative of the x, y coordinates of the scintillation. Another signal indicates the energy of the scintillation. By comparing this signal with one or more predetermined references, the camera 20 can determine if the associated pair of x, y coordinate signals represents a plurality of simultaneous flashes, or stray radiation, or for some other reason is undesirable. In conventional gamma cameras, this comparison produces an unblanking signal to enable only desirable x, y coordinate signals to be displayed on the display device 52. The unblanking signal is termed here unblanking z signal.

In a conventional camera 20, each pair of analog x, y coordinate signals is directly conveyed to the display device 52 which commonly is of the oscilloscope type cathode ray tube.

If an appropriate unblanking z signal is produced, it is also conveyed to the display device 52. As a result, the electron beam of the cathode ray tube will excite a small region or dot of the persistence phosphor at a location corresponding to the x, y coordinates represented. A plurality of small dots of phosphor form the image to be examined.

It will be noted that in the embodiment according to FIG. 1, the x, y and z signals are not applied directly to the display device 52, but to the processing unit 50. It will also be noted that the output signals X', Y', unblank Z' of the processing unit 50 are used to control the display device 52. That is, the design of the conventional scintillation camera 20 remains unchanged. Only the unit 50 is interposed. The output signals x, y, z of the camera 20 are introduced into this additional unit 50 to form input or display control signals X', Y', unblank Z' coordinates therefrom. The unit 52 electronically provides a square field of view which is maintained at a fixed angular orientation with respect to the X', Y' coordinate system when the camera 20 is swiveled about the Z' axis.

Figure 2:
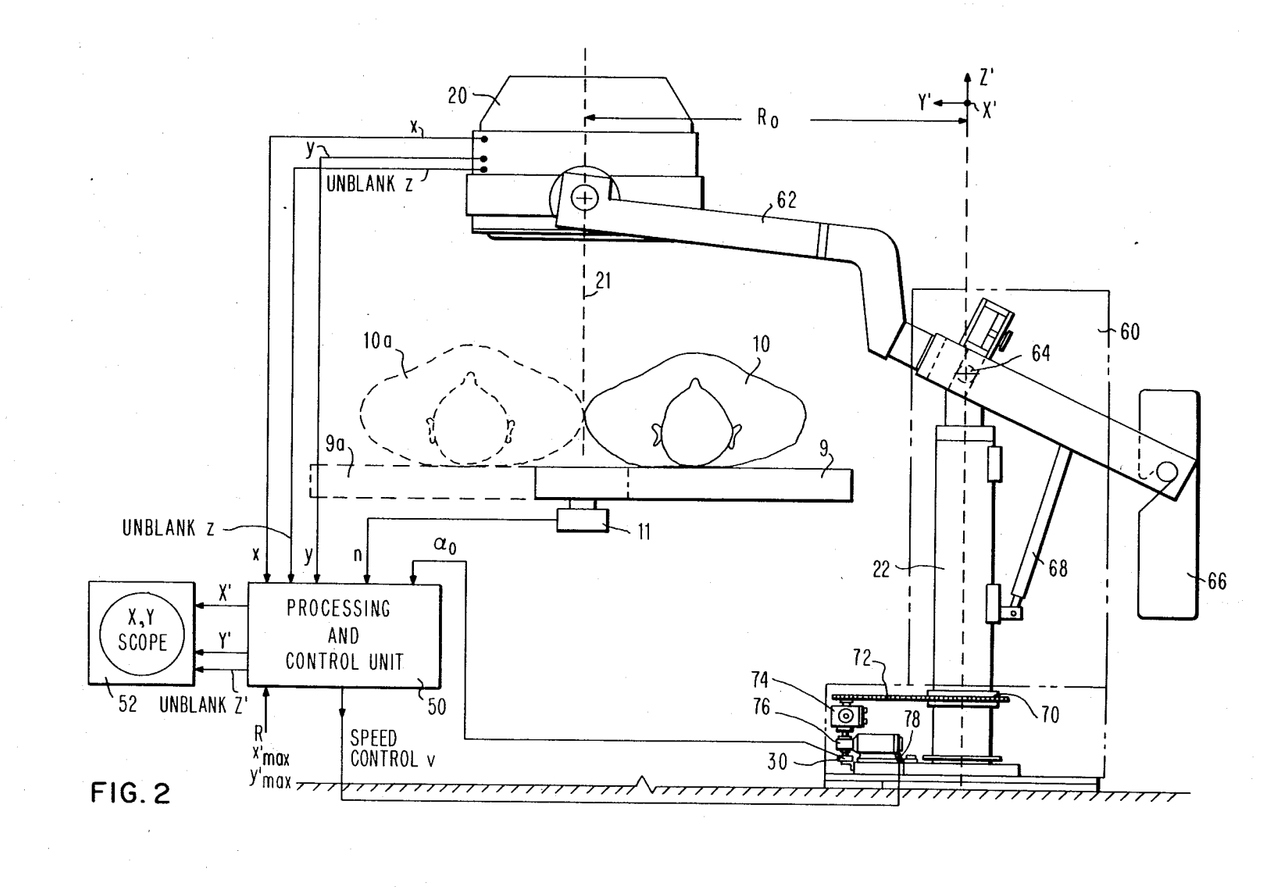
FIG. 2 is a side view of a whole-body scanning apparatus according to a second embodiment of the invention.

In FIG. 2, another nuclear imaging apparatus or arcscanner is illustrated. In this embodiment, the same or related parts and elements are provided with the same reference numerals as in FIG. 1.

According to FIG. 2, a C-stand 60 for a large field of view camera 20 is used. The C-stand 60 may be of a design which is disclosed by Werner J. Haas and Frank C. Scribano in U.S. Pat. No. 4,417,143. The C-stand 60 contains a column 22 which is rotatable about the vertical Z' axis of the fixed system X', Y', Z'. The C-stand 60 supports a detector arm 62 which is rotatable about a horizontal axis 64 intersecting the Z' axis. One end of the detector arm 62 carries the camera 20, whereas the other end is provided with a balancing weight 66. A spring means such as a gas spring 68 is provided for keeping the detector arm 62 in a balanced position. The radial distance of the camera center line 21 from the pivot axis or Z' axis of the C-stand 60 is designated by $R_0$. The distance $R_0$ between the column 22 as pivot and the center of the camera 20 may be e.g. 100 cm.

The patient 10 is again positioned on a table top 9. The position of the table top 9 with respect to the Y' direction is determined by a position encoder 11. Two different end positions of the table top 9 are illustrated. The first end position is illustrated in solid lines. The second position of the patient 10a and of the table 9a is illustrated in broken lines. It will be noted from the position of the center line 21 of the camera 20 that the whole width of the patient 10 may be relocated underneath the center of the camera 20.

The mechanism for swiveling the camera 20 around the Z' axis comprises a column drive sprocket 70 which is contained in the C-stand 60 and fastened to the circumference of the lower portion of the column 22. The sprocket 70 is driven by a chain drive 72 which in turn is operationally connected to a gear reducer 74. The gear reducer 74 in turn is driven by a gear motor 76, the speed of which can be controlled via an appropriate signal v at its speed control input 78. Attached to the shaft of the gear motor 76 is a shaft encoder 30 which provides the column position signal $\alpha_0$.

The x and y signals of the camera 20 and the position signals n and $\alpha_0$ are applied to a processing and control unit 50. This unit 50 additionally receives information about the radial distance $R_0$ and two maximal values $x'_{max}$ and $y'_{max}$. The unit 50 issues output signals X', Y' and unblank Z' which are applied to an x, y scope 52. It also issues a speed control signal v which is applied to the control input 78 of the gear motor 76.

In an examination of the patient 10, the table top 9 is first brought into a desired table Y' position. Then the motor 76 contained in the C-stand 60 works on the gear reducer 74, the chain drive 72 and the sprocket 70, thereby swiveling the C-stand 60 and the column 22 including the camera 20 around the Z' axis. As a result, the camera 20 scans along an arc-shaped path which is located over the patient 10 (whole body arc scan), and images are taken. When such a pass along a curved path close to the patient 10 is completed, the table top 9 is moved one step in Y'-direction, and the next scanning pass will commence. This is continued until a predetermined number n = 1, 2, ... k of passes is completed and the patient 10 is completely scanned.

Figure 3:
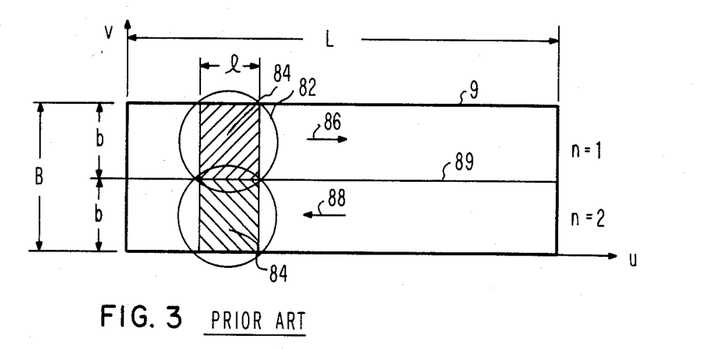
FIG. 3 is a scanning pattern of a nuclear imaging apparatus according to the prior art.

In FIG. 3, a scanning method according to the prior art is illustrated. According to this method, a scintillation camera produces a circular field of view 82. This field of view 82 is linearly scanned across an area or object to be examined, such as a table top 9 carrying a patient (not shown). It is assumed that the object is scanned in two linear passes n=1 and n=2. Scanning is performed in u direction which is parallel to the longitudinal direction of the object. In each position u, only a rectangular portion 84 of the circular field of view 82 is electronically screened and released for recording. This rectangular field 84 has a width b and a length l. That is, the surplus portions, which are limited by arcs, are eliminated electronically. The rectangular image is displayed and/or recorded.

In performing this conventional method, the rectangular field of view 84 is brought into a starting position or first pass position at the left edge of the area 9 to be examined. In the first pass n=1, the rectangular field of view 84 is scanned along the complete scan length L in the direction of the arrow 86 until it arrives at the right edge of the area 9. Subsequently, the camera 20 is shifted by the width b in (−v) direction, or the bed 9 is shifted in (+v) direction by the width b, in order to assume a second pass position.

Subsequently, in the second pass n=2, the rectangular field of view 84 is scanned back into a position at the left edge of the examination area 9. Scanning is now along the arrow 88. The total scan width is B=2b.

During the scanning operation, the upper side of the masked field of view 84 in the second pass n=2 is positioned adjacent to the lower side of the field of view 84 in the first pass n=1, and both of these sides are parallel to the u direction. At the location where both linear scanning areas about, in the recordation of the images a disturbing line 89 appears which is called "zipper line". This zipper line 89 is caused by the fact that along this line an information gap or overlap exists. In other words, at the border between the areas covered by the first pass n=1 and the second pass n=2, an irritating zipper line 89 is generated in the displayed image because of either a slight gap or overlap between the areas covered by each pass.

Figure 4:
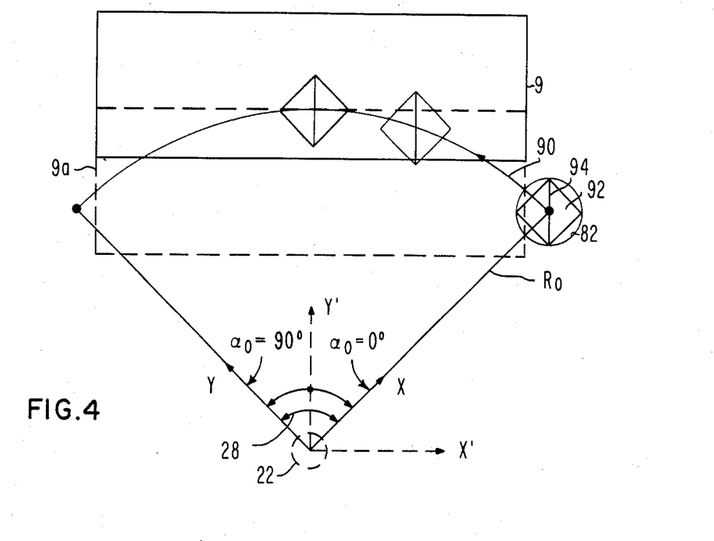
FIG. 4 is a scanning pattern of a nuclear imaging apparatus according to this invention.
Figure 5:
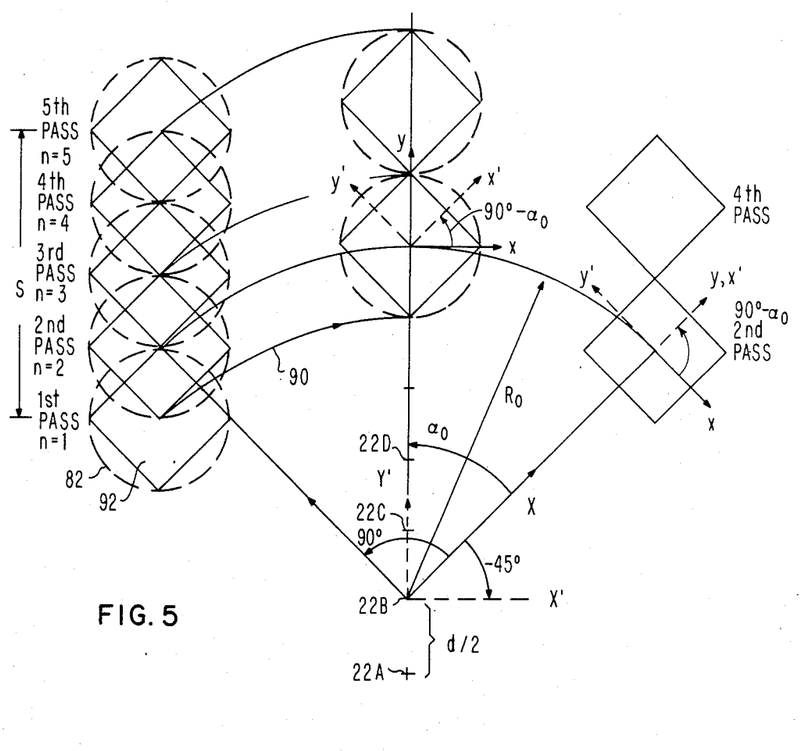
FIG. 5 is a schematic illustration showing the orientation of a patient table with respect to a plurality of arc-shaped scanning paths.

The scanning method illustrated in FIGS. 4 and 5 avoids such zipper line 89.

In former methods, there is a trade-off between the scan width b and the sensitivity of a conventional scintillation camera. With the scan width b chosen large, the scanning field of view 84 has to be narrow (l small) and the scanning speed has to be slow, in order to integrate a sufficiently large number of radiation counts. With the choice of a large length l of the scanning field of view 84, allowing for a higher scanning speed, the scan width b has to be small. Consequently, a high scanning speed and a large scan width b cannot be simultaneously achieved in the formerly used method.

In FIGS. 4 and 5, the scanning method according to this invention is illustrated which avoids the conventional trade-off between scan width and sensitivity and also the zipper line between areas covered by adjacent passes.

According to FIG. 4, the swiveling axis of the column 22 is again the Z' axis of an orthogonal coordinate system X', Y', Z' which is fixed in space. A patient table 9 is provided having its longitudinal axis located parallel to the X' axis. A second fixed coordinate system X, Y is defined to be inclined by 45° with respect to the fixed system X', Y'. The X-axis of this second coordinate system defines the angular position $\alpha_0 = 0°$. In a rest position at $\alpha_0 = 45°$, the arm 62 of the camera 20 extends perpendicularly to the long side of the patient table 9, that is in Y' direction. The Y' direction is again the shift direction of the table 9. The shifted table 9a is indicated in broken lines. A single pass is preferably performed by a swivel (see double arrow 28) from $\alpha_0 = 0°$ through $\alpha_0 = 90°$ or vice versa. The scan path of the camera center is designated by 90. The angle $\alpha_0$ is measured from the X-axis.

In contrast to FIG. 3, the field of view 82 of the camera is masked such that particularly a square field of view 92 is enclosed. The orientation of the masked field of view 92 is fixed during the swivel of the camera 20 along the scan path 90. With each rotation of the camera arm 62 by an angle of $+d\alpha_0$, the masked field of view 92 is counter-rotated by $-d\alpha_0$. This results in the aforementioned alignment of the masked field of view 92 throughout the scan. In FIG. 4 three camera positions are illustrated on the scan path 90. It will be noted that in each camera position the diagonal 94 of the field of view 92 is parallel to the Y' axis. This feature is achieved by coordination transformation in the unit 50.

According to FIG. 5, multiple passes are performed. Each of these passes is detained after having shifted the patient table 9 by a given distance towards (or alternately away from) the column 22. Instead, the column 22 may have been shifted toward the patient table 9.

As illustrated in FIG. 5, the area to be examined is scanned in several arc-shaped passes with a scintillation camera 20 having a circular field of view 82. In the present case the field of view 82 is again electronically confined to a rectangular field of view 92 which is specifically quadratic. It will be noted again that the quadratic or square field of view 92 is inclined by 45° with respect to the X', Y' system. In other words, one of the two diagonals of the quadratic field of view 92 is arranged parallel to the Y' axis. In the present case, there are not only two passes (see FIG. 3), but a total of five passes n=1, 2 ... 5 performed. In the first pass n=1, the aforementioned diagonal of the masked field of view 92 may coincide with the left edge of the region of interest 9. Scanning starts in this left pass portion. The field 92 keeping its orientation is scanned along the curved path 90. The position of the column 22 is denoted by 22A. Before the second pass n=2, the scintillation camera 20 (now at the right side) is assumed to have been shifted in Y' direction by half the diameter d of the quadratic field 92 see column position 22B. The same happens in each of the third, fourth and fifth passes n=3, n=4, and n=5, respectively.

It will be noted from FIG. 5 that adjacent areas are scanned in opposite directions. It will also be noted that adjacent scanning areas overlap. The scan width S is defined as the total width of a multiple pass scan within which adjacent scanning areas overlap. Considering five passes n=1, 2, ... 5, the five pass scan width S equals twice the diagonal diameter d of the imaging field of view 92: S=2d. Due to this overlap, zipper lines are avoided.

It should be mentioned that instead of five passes n=1, 2, ... 5, a total of e.g. only three passes (k=3) can be performed, namely the passes n=2, n=3, and n=4. Also in this case the scanned areas of adjacent scanning areas overlap. The scan width S is S=d. Also, other values of k may be selected.

By application of a square field of view 92, optimum use of the available detector area and thus of the available field of view 82 is made. By having rotated the scanning field of view 92 by 45° with respect to the system X', Y', the total field of view diameter of the camera detector is covered. This results in the optimum use of the available detector area.

It has been mentioned that in the preferred embodiments either three passes n=2, 3, 4 or five passes n=1, 2, ... 5 may be performed, each pass with a separation of ½ of the diameter d of the field of view. This guarantees a constant sensitivity over the scan width S. As mentioned before, this approach of overlapping passes eliminates any zipper line.

In FIG. 5, coordinates x, y, and x', y', as well as coordinates X, Y, and X', Y' are defined. The coordinates x, y describe the position of a gamma event in the gamma camera 20, in the conventional way. In other words, the positioning electronics of the gamma camera 20 will conventionally measure the location of a gamma event in x, y coordinates. The coordinates x', y' described the location of the gamma event in a rotated camera system. The rotation is such that the lower corner of the field of view 92 in all angle positions $\alpha_0$ points in $-Y'$ direction. The coordinates X, Y are the position of the gamma event in a coordinate system which is rotated by $+45°$ with respect to the X', Y' system. $R_0$ is the radial distance of the C-stand pivoting axis Z' to the camera center. $\alpha_0$ is the angle of the camera swivel. It is variable between 0° and 90°.

In order to obtain a field of view 92 which is always oriented by 45° with respect to the X', Y' coordinate system and which is enclosed by a square mask, a coordinate transformation system is used. In other words, the unit 50 produces the rotated (hatched) field of view 92 electronically by eliminating the four portions of the field of view 82 that are limited by arc portions. The mask is electronically defined by thresholds $x'_{max}$, $y'_{max}$, as will become apparent later.

Figure 6:
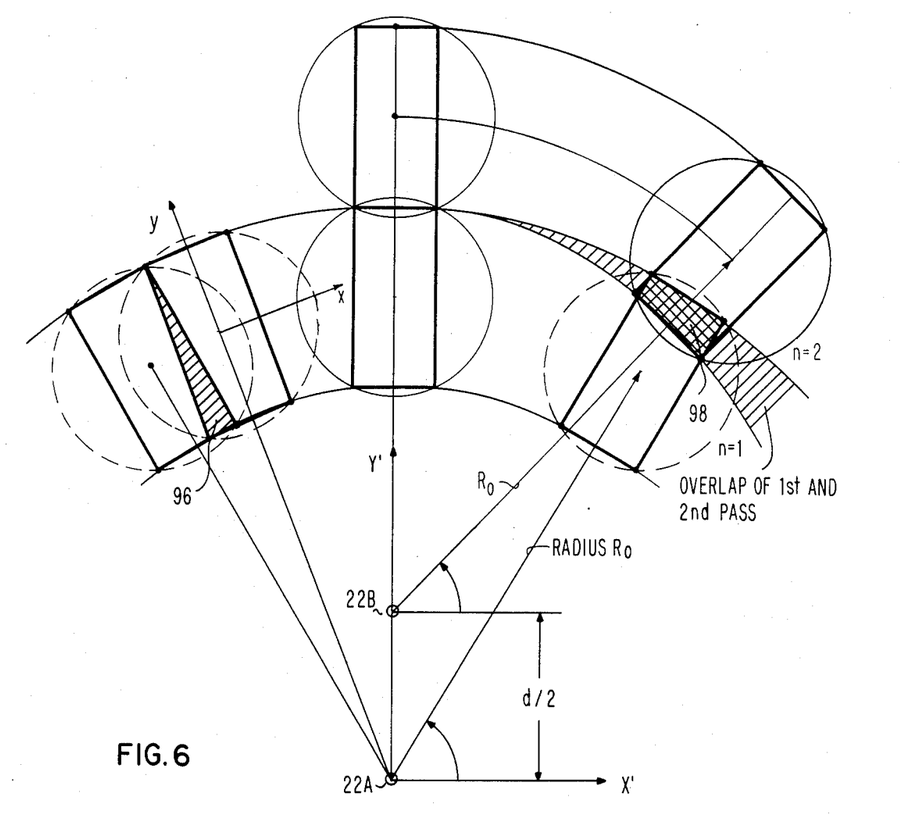
FIG. 6 is a scanning pattern incorporating a rectangular field of view for illustration of sensitivity and overlap problems.

FIG. 6 illustrates sensitivity problems (left side) and overlap problems (right side) which would occur when generally a rectangular and not particularly a square field of view is used which is not oriented in the manner described above. Due to the superposition of the two coordinate systems of the camera 20 and the column 22, data acquisition is complicated. On the left side of FIG. 6, a rectangular field of view scanning along a first path in a first pass n=1 is illustrated. The hatched wedge-shaped area 96 indicated that there is a decrease in sensitivity with increasing radial distance within each pass n.

On the right side of FIG. 6, a rectangular field of view in a first pass n=1 and in the adjacent second pass n=2 is illustrated. The hatched area 98 indicates that there is an overlap of the scanned areas in multiple pass scans. This overlap would also result in a complex design of the circuitry for data acquisition. The method for whole body arc scan data acquisition illustrated in FIG. 5 avoids these complications as well as the aforementioned disadvantages of the linear whole body scan method.

Figure 7:
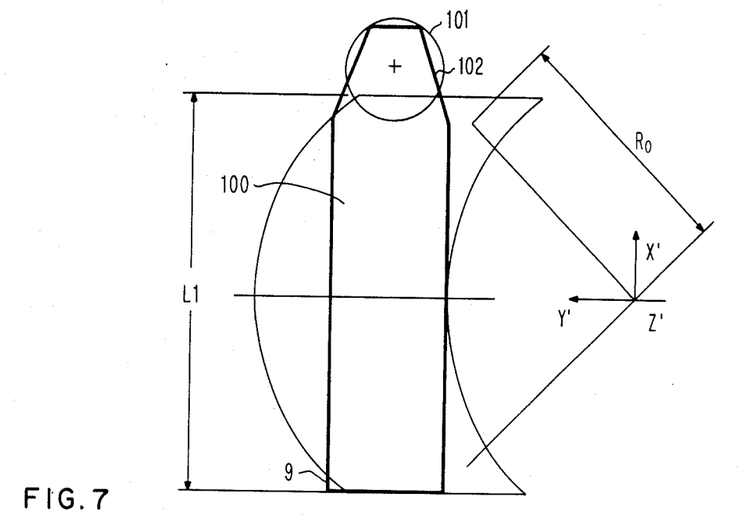
FIG. 7 is a diagram showing composition of two scanning patterns.

In FIG. 7 is illustrated that the arc scanner can scan a large area 100 of a patient table top 9. The scanned area may be sufficient to cover as much as e.g. 95% of a large patient's size, depending on the dimensions of the scanner (e.g. scan length L1). In order to extend the imaged area, a single image 101 may be added. As illustrated, this image 101 may cover the patient's head resting on the head support 102 of the table top 9. Alternatively, such a single image can also be taken from the patient's feet. Such an additional image 101 may be obtained after shifting either the column laterally in X' direction and maintaining the table position, or by maintaining the table position and shifting the table top in $(-X')$ direction.

Figure 8:
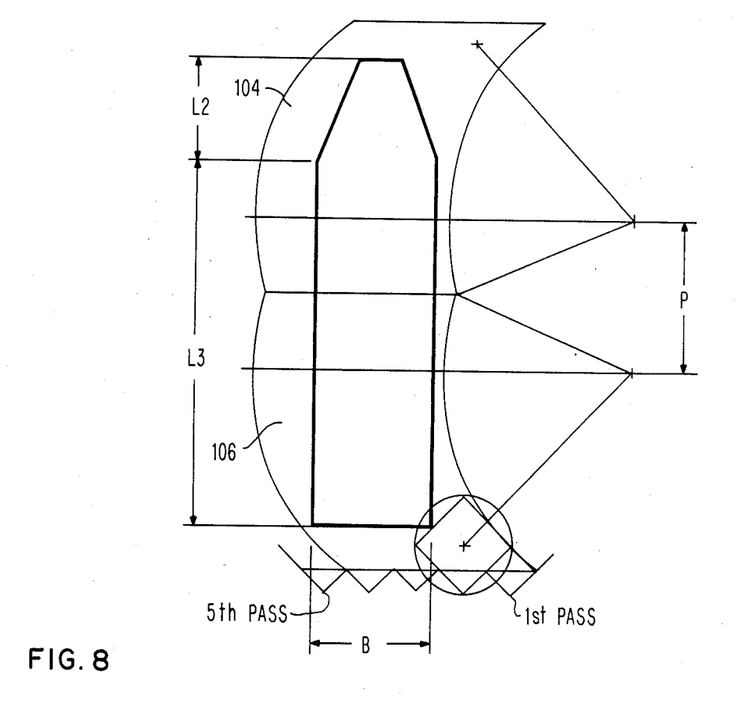
FIG. 8 is another diagram illustrating composition of two scanning patterns.

In FIG. 8 is illustrated that an extension of the imaged area may be obtained by appropriate composition of two multiple pass scans 104 and 106. Each of these scans 104 and 106 may comprise less than 90°, as illustrated. Also in this case, a lateral shift of the column 22 in X' direction or a longitudinal shift of the table top 9 in $(-X')$ direction is required. The shift is designated by P. In FIG. 8 is assumed that (L2+L3) is larger than L1 (FIG. 7).

The above-mentioned coordinate transformation makes use of the following equations:

$$X = x' + R_0 \cos \alpha_0$$
$$Y = y' + R_0 \sin \alpha_0 \tag{1}$$

and $$x' = x \sin \alpha_0 + y \cos \alpha_0$$
$$y' = -x \cos \alpha_0 + y \sin \alpha_0 \tag{2}$$

One advantage of this approach is that equations (1) and (2) can be realized electronically on-line by using analog or digital circuitry (FIG. 9) without requiring a mass memory and any post processing equipment for back-transformation.

As mentioned above, during a sweep (scan, pass), the orientation of the masked field of view of the camera 20 is kept fixed with respect to the coordinates X', Y' of the stand, i.e. the masked field of views are aligned throughout the scan. This eliminates the sensitivity problem shown in FIG. 6, left side. This is accomplished by using (x', y') instead of (x, y) and the condition:

If $$|x'| \geq x'_{max} \text{ and/or } |y'| \geq y'_{max} \tag{3}$$

then delete the event,
which would otherwise lead to an image point. This can be done by deactivating the unblank z signal generated by the camera 20. The values $x'_{max}$ and $y'_{max}$ represent herein preset values describing the four borders of the screened field of view 92. For a square image 92, $$|x'|_{max} = |y'|_{max} \tag{4}$$

For an appropriate, orthogonal display of the scan image on a scope or TV-monitor, the X, Y system is rotated by $-45°$ into the X', Y' system (FIG. 5) by the following equations:

$$X = X \cos 45° - Y \sin 45° = \text{const}(X - Y)$$
$$Y = X \sin 45° + Y \cos 45° = \text{const}(X + Y). \tag{5}$$

The position of a gamma event in X', Y' coordinates can be displayed directly on a x, y scope, or it can be written into a memory for documentation and post-processing.

Referring again to FIG. 5, the following three remarks can be made:
(a) The patient table is oriented at 45° with respect to the X, Y system for multiple passes (FIG. 5, left side) and a square field of view is used by appropriate choice of $x'_{max}=y'_{max}$. This makes optimum use of the available camera detector area. As a consequence, two passes with a shift of one large field of view diameter (e.g. pass 2 and 4 on the right side of FIG. 5) do not overlap as long as the range of $\alpha_0=0°$ to 90° is not exceeded. Thus, the overlap problem explained in FIG. 6, right side, is solved.

(b) In order to maintain constant sensitivity over the entire scan width, three overlapping passes are performed (instead of 1 pass as in the left side of FIG. 6), and up to five passes (instead of two passes as in the right side of FIG. 6), each with a shift of d/2, where d is the diameter of the field of view. There is no disadvantage in terms of scanning time as long as the same number of counts integrated over all passes is maintained. There is, on the other hand, the advantage that zipper lines are eliminated. The table shift in Y' direction is taken care of by monitoring the table position n.

(c) The alignment of the masked field of view described under (a) has as a consequence that the scanning speed along the patient table varies with the range $\alpha_0$. In order to maintain a constant sensitivity over the entire angular range, the scanning speed may be controlled according to $$\frac{d}{dt} = \frac{const.}{\sin(\alpha_O + 45°)} \quad (6)$$

Figure 9:
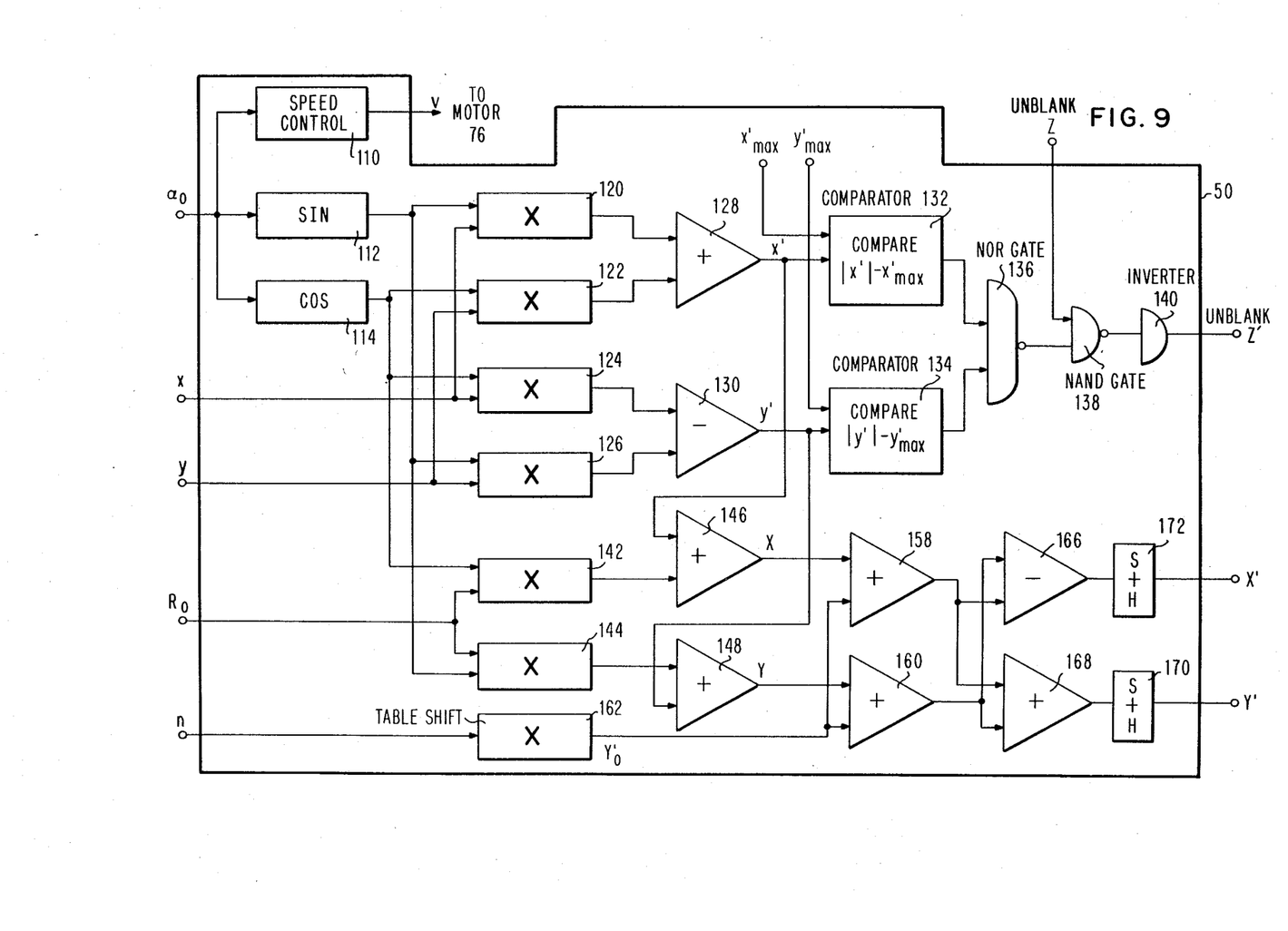
FIG. 9 is a block circuit diagram of a processing and control unit for generating a square field of view and for issuing coordinate signals for display on a display device.

This may be done by using the motor control input 78 in FIG. 2 and the speed control circuit 110 in FIG. 9.

In FIG. 9 an embodiment of the processing unit 50 is illustrated. The processing unit 50 works according to equations (1)–(5). It contains a speed control device 110, a sine function generator 112 and a cosine function generator 114 which are supplied by the angular position value $\alpha_0$.

In a first stage, the coordinate signals $x'$ and $y'$ are generated according to equation (2). This first stage contains four multiplication members 120, 122, 124 and 126, an addition member 128 and a subtraction member 130. The subtraction member 130 subtracts the expressions $y \sin \alpha_0$ and $x \cos \alpha_0$ from each other, thereby obtaining the coordinate signal $y'$. The addition member 128 adds the expression $x \sin \alpha_0$ and $y \cos \alpha_0$ to each other, thereby obtaining the coordinate signal $x'$.

These signals $x'$ and $y'$ are transmitted to comparators 132 and 134, respectively, which belong to a second stage. In this second stage, an unblank $Z'$ signal is generated according to equation (3). For this purpose to the comparator 132 is additionally supplied the predetermined maximum value $x'_{max}$, and to the comparator 134 is additionally supplied a predetermined maximum value $y'_{max}$. These maximum values $x'_{max}$ and $y'_{max}$ define the borders of the rectangular field of view 92. Since this field 92 is square, these values are equal to each other, see equation (4).

The comparators 132 and 134 determine whether the difference $(|x'|-x'_{max})$ and $(|y'|-y'_{max})$, respectively, is smaller than zero. The comparator 132 delivers a "low" level signal as long as the coordinate signal $x'$ is smaller than the predetermined maximum value $x'_{max}$. The comparator 134 correspondingly delivers a "low" level signal as long as the coordinate signal $y'$ is smaller than the predetermined value $y'_{max}$. The output signals of the comparators 132 and 134 are transmitted to a NOR gate 136, which also belongs to the second stage. This NOR gate 136 will deliver a "high" level output signal as long as both coordinates $x'$, $y'$ are located within the square field of view 92.

The output signal of the NOR gate 136 is applied to one of two inputs of a subsequent NAND gate 138. To the other input is applied the unblank signal z from the camera 20. If both input signals are "high", the output signal of the NAND gate 138 is "low" which is then converted to a "high" level signal by means of an inverter gate 140. The output of the gate 140 is used as the unblank signal $Z'$ and passed to the x, y scope 52 or to another display advice.

The unit 50 also contains a third stage comprising two multiplication members 142 and 144, and two summation members 146 and 148. The members 146 and 148 generate coordinate signals X and Y according to equation (1). The multiplication members 142, 144 generate expressions $R_0 \cos \alpha_0$ and $R_0 \sin \alpha_0$, respectively, which are supplied to the addition members 146 and 148, respectively. The output signals $x'$ and $y'$ from the members 128 and 130, respectively, are also supplied to the addition members 146 and 148, respectively. In the addition member 146, the input signals are added to form an output signal which is proportional to the coordinate signal X. In the addition member 148, the input signals are added such that the output signal is proportional to the coordinate signal Y.

These output signals X, Y are transmitted to a fourth stage, in which the shift position of the table top 9 in Y' direction is taken into account. This next stage contains two summation members 158 and 160, and a table shift transformer or correlator 162. The table shift transformer 162 converts the coded table position information n into a corresponding analog magnitude $\frac{1}{2}Y_0'$. In the summation members 158 and 160, the table position signal $\frac{1}{2}Y_0'$ ($Y_0'$ defining the position of the table top 9 in Y' direction) is added to the output signals of the addition members 146 and 148, respectively.

The last stage works according to equation (5). It comprises a difference or subtraction member 166 and an addition member 168. Both members 166, 168 are supplied with the output signals of the summation members 158, 160. The subtraction member 166 furnishes basically the output signal X', whereas the addition member 168 issues basically the output signal Y' which includes the table position $Y_0'$. Both coordinate signals X', Y' describe the location of a gamma event in an orthogonal coordinate system which is located at the swiveling axis Z' of the camera 20 and which is fixed in space. The output signals X', Y' of the members 166 and 168 are transmitted to sample-and-hold circuits 170 and 172, respectively. At the outputs of the circuits 170 and 172, the stored output signals X' and Y', respectively, are obtained. That is, the sample-and-hold circuits hold the X' and Y' signals until a subsequent scintillation event in the detector 20 produces a new set of x, y signals which are applied to the members 120, 122, 124 and 126. The signals X', Y' are imaged in a conventional way on the (x, y)-scope 52 and/or recorded in a conventional way in the recording device 54, if an unblank signal Z' is generated at the output of the inverter 140.

While the forms of the nuclear imaging apparatus herein described constitute preferred embodiments of the invention, it is to be understood that the invention is not limited to these precise forms of assembly, and that a variety of changes may be made therein without departing from the scope of the invention.

What is claimed is:

1. A nuclear imaging apparatus for producing images of an object under examination which emits nuclear radiation, comprising in combination
    (a) a scintillation camera for receiving said radiation and for determining the locations of scintillation events generated by said nuclear radiation, said scintillation camera issuing x and y coordinate signals corresponding to said locations and issuing z unblank signals corresponding to the intensity of said scintillation events;
    (b) display means having a screen for displaying image points under the control of said z unblank signals on screen locations determined by said x and y coordinate signals;
    (c) means for generating a relative movement between said scintillation camera and said object along a first and a second arc-shaped scanning path;
    (d) transferring means generating a shift movement between said object and said scintillation camera from a first pass position to a second pass position along a linear shift direction, each of said first and second pass positions being associated with said first and second scanning paths, respectively; and
    (e) electronic means for enclosing a square field of view when said imaging points are displayed on said display means, said electronic means being fed by said x and y coordinate signals and supplying the input of said display means with input signals such that said square field of view maintains a fixed angular orientation with respect to a fixed coordinate system during each of said passes.

2. The apparatus according to claim 1, wherein said means for generating a relative movement between said scintillation camera and said object comprises means for pivoting said scintillation camera about a rotation axis, whereby said object is in a fixed position.

3. The apparatus according to claim 2, wherein said rotation axis is formed by a column which is positioned vertically and which supports said camera.

4. The apparatus according to claim 2, wherein said pivoting means is designed for rotations of said camera from 0° to 90° with respect to a predetermined axis of said fixed coordinate system which system is fixed in space.

5. The apparatus according to claim 4, wherein said predetermined axis makes a 45° angle with said shift direction.

6. The apparatus according to claim 4, wherein said square field of view contains a diagonal which is moved in positions 45° offset from to said predetermined axis of said fixed coordinate system when said camera pivots about said rotation axis.

7. The apparatus according to claim 3, wherein said rotation axis is fixed in space, and wherein said object is movable along said linear shift direction.

8. The apparatus according to claim 1, wherein said object is positioned on a table top, the longitudinal axis of which is positioned perpendicularly to said shift direction.

9. The apparatus according to claim 1, wherein said transferring means is provided for shifting said object by equal steps into a plurality of predetermined pass positions, and wherein the shifting distance between two adjacent pass positions corresponds to half the diagonal diameter of said square field of view.

10. The apparatus according to claim 1, wherein said electronic means comprises transformation means for generating rotated coordinate signals $x'$, $y'$ defined by the transformation equations:

$$x' = x \sin \alpha_0 + y \cos \alpha_0 \text{ and}$$

$$y' = -x \cos \alpha_0 + y \sin \alpha_0,$$

wherein x and y are said coordinate signals defining the locations of said scintillation events and wherein $\alpha_0$ is an angle defining the angular position of said camera, further comprising means for suppressing an image point on said display screen if said rotated $x'$ coordinate signal exceeds a predetermined maximum value representing a first edge of said square field of view, and further comprising means for suppressing an image point on said display screen if said rotated $y'$ coordinate signal exceeds a predetermined maximum value representing a second edge of said square field of view, said second edge being positioned perpendicularly to said first edge.

11. A method for producing images of an object under examination by means of a scintillation camera, which generates a rectangular field of view on a display device, comprising the steps of:
    (a) scanning said object in a first arc-shaped pass;
    (b) moving said camera and said object relative to each other in a linear shifting direction;
    (c) scanning said object in a second arc-shaped pass which is parallel to said first pass,
whereby the field of view of said first and second passes overlap each other and maintain their orientation with respect to a fixed coordinate system during said first and second pass.

12. The method according to claim 11, wherein an area of interest containing said object is scanned in five parallel passes, and whereby the field of view of any two neighboring passes overlap each other.

13. The method according to claim 11, wherein an area of interest containing said object is scanned in a plurality of parallel arc-shaped passes, whereby the fields of view of any two neighboring passes overlap each other.

* * * * *